United States Patent [19]

Kristiansen et al.

[11] Patent Number: 4,892,880

[45] Date of Patent: Jan. 9, 1990

[54] PESTICIDAL PYRIDYLTHIADIAZOLES

[75] Inventors: Odd Kristiansen, Möhlin; Jozef Drabek, Oberwil, both of Switzerland

[73] Assignee: Ciba-Geigy Corporation, Ardsley, N.Y.

[21] Appl. No.: 4,743

[22] Filed: Jan. 7, 1987

Related U.S. Application Data

[63] Continuation of Ser. No. 570,711, Jan. 13, 1984, abandoned.

[30] Foreign Application Priority Data

Jan. 19, 1983 [CH] Switzerland .............................. 300/83

[51] Int. Cl.$^4$ .................... C07D 417/04; A01N 43/40
[52] U.S. Cl. .................................... 514/342; 546/277
[58] Field of Search ................ 546/280, 277; 514/342; 548/136

[56] References Cited

U.S. PATENT DOCUMENTS

| | | | |
|---|---|---|---|
| 2,733,245 | 1/1956 | Ainsworth | 546/277 |
| 2,744,908 | 5/1956 | Young | 548/136 |
| 3,287,463 | 11/1966 | Rufenacht | 548/136 |
| 3,903,099 | 9/1975 | Rathgeb | 548/136 |
| 4,518,601 | 5/1985 | Kristiansen et al. | 514/340 |

OTHER PUBLICATIONS

Lin et al., Chem. Abstracts, vol. 93, (17) 168, 204p Oct. 27, 1980.

Ikeda et al., Chem. Abstracts, vol. 72, (17), abst. No. 90, 374p Apr. 27, 1970.
Chemical Abstract 73, 56031k, p. 322 (1970).

*Primary Examiner*—Alan L. Rotman
*Attorney, Agent, or Firm*—Kevin T. Mansfield; Edward M. Roberts

[57] ABSTRACT

The invention relates to pesticidal compositions which contain 2-(3-pyridyl)-1,3,4-thiadiazoles or 5-(3-pyridyl)-1,2,4-thiadiazoles of the formula

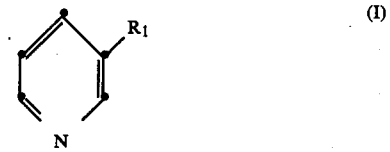

(I)

wherein $R_1$ is

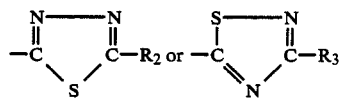

and each of $R_2$ and $R_3$ is hydrogen or $C_1$–$C_4$alkyl, to the novel compounds of the formula I themselves, to the preparation thereof, and to the use thereof in pest control.

5 Claims, No Drawings

PESTICIDAL PYRIDYLTHIADIAZOLES

This application is a continuation of application Ser. No. 570,711, filed Jan. 13, 1984, now abandoned.

The present invention relates to pesticidal compositions which contain a 2-(3-pyridyl)-1,3,4-thiadiazole or 5-(3-pyridyl)-1,2,4-thiadiazole as active component, to the use of said compositions in pest control, and also to novel 2-(3-pyridyl)-1,3,4-thiadiazoles and 5-(3-pyridyl)-1,2,4-thiadiazoles and to the preparation thereof.

The 2-(3-pyridyl)-1,2,3-thiadiazoles and 5-(3-pyridyl)-1,2,4-thiadiazoles of this invention have the formula I

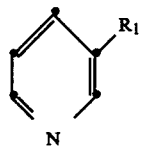
(I)

wherein $R_1$ is

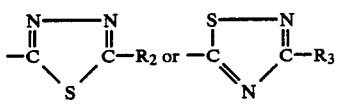

and each of $R_2$ and $R_3$ is hydrogen or $C_1$–$C_4$alkyl, preferably $C_1$–$C_3$alkyl.

The alkyl groups $R_2$ and $R_3$ may be straight chain or branched and are methyl, ethyl, n-propyl, isopropyl, n-butyl, isobutyl, sec-butyl or tert-butyl.

Particularly interesting novel compounds falling within the scope of formula I are those in which $R_1$ is as defined above, $R_2$ is hydrogen or $C_1$–$C_4$alkyl, preferably $C_1$–$C_3$alkyl, and $R_3$ is $R_1$–$C_4$alkyl, preferably $C_1$–$C_3$alkyl.

On account of their pesticidal action, particularly preferred compounds of the formula I are those in which $R_1$ is

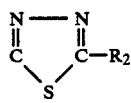

and $R_2$ is hydrogen or $C_1$–$C_3$alkyl.

The compounds of formula I can be prepared by methods which are known per se [q.v. J. Am. Chem. Soc. 80, 5201 (1958); J. Het. Chem. 1319 (1981); and J. Org. Chem. 45, No. 19, 3750 et seq. (1980)], for example as follows:

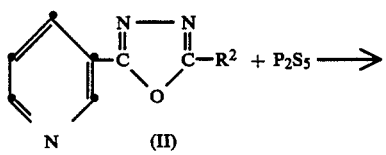

compound of formulaI
wherein $R_1$ is

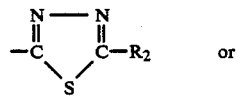

-continued

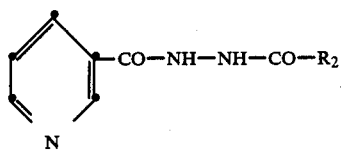

$$\begin{array}{c}\text{pyridyl}\end{array} \overset{S}{\underset{\|}{C}}-N=\overset{R_3}{\underset{\|}{C}}-N(CH_3)_2 \xrightarrow{\text{in the presence of hydroxylamine-O-sulfonic acid}}$$
(IV)

compound of formula I, wherein $R_1$ is

In the formulae II to IV above, $R_2$ and $R_3$ are as defined for formula I.

Processes 1 and 2 are carried out under normal pressure and in the temperature range from 5° to 180° C., preferably from 20° to 160° C., and optionally in a solvent or diluent.

Examples of suitable solvents or diluents are: ethers and ethereal compounds such as diethyl ether, diisopropyl ether, dioxan, tetrahydrofuran; aliphatic and aromatic hydrocarbons, preferably benzene, toluene, xylenes; and ketones such as acetone, methyl ethyl ketone and cyclohexanone.

Most of the starting materials of the formulae II, III and IV are known or, if they are novel, can be prepared by methods similar to known ones.

Thus, for example, the 2-pyridyloxdiazoles of the formula II can be obtained by reacting nicotinic acid hydrazide with ortho-esters [q.v. J. Am. Chem. Soc. 77, 1148 (1955)]. The 2-acylnicotinic acid hydrazides of the formula III can be obtained by reacting nicotinic acid hydrazide with corresponding reactive carboxylic acid derivatives [q.v. J. Am. Soc. 75, 1933 (1953)]. The N'-(3-pyridyl)thiocarbonyl-N,N-dimethylamidines of the formula IV can be obtained by reacting thienyl nicotinamide of the formula V with corresponding amide acetals of the formula VI, wherein $R_3$ is as defined above [q.v. J. Org. Chem. 45, No. 19, 3751 (1980)].

It is known from published European patent application 0 062 612 and U.S. patent specification No. 4 260 765 that substituted 3-pyridylthiazolines and 3-pyridylthiazoles have insecticidal activity against sucking insects such as aphids. Further, 5-(3-pyridyl)-1,2,4-thiadiazole and the preparation thereof is disclosed in J. Org. Chem. 1980, Vol. 45, p. 3751. However, no information relating to the biological activity of this compound is disclosed in this reference. Surprisingly, it has been found that the class of 3-pyridylthiadiazoles proposed in this invention, which are novel except for the previously mentioned 5-(3-pyridyl)-1,2,4-thiadiazole, have good pesticidal, especially good aphicidal, properties.

The compounds of formula I are suitable for controlling pests of animals and plants and soil pests, for example for controlling insects of the order Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera, and also phytopathogenic mites and ticks of the order Acarina.

In particular, the compounds of formula I are suitable for controlling plant-destructive insects, especially plant-destructive feeding insects, in ornamentals and crops of useful plants, chiefly in cotton plantations (e.g. *Spodoptera littoralis* and *Heliothis virescens*) and in vegetable crops (e.g. *Leptinotarsa decemlineata* and *Myzus persicae*).

In this connection, particular attention is drawn to the fact that the compounds of formula I have both a strongly pronounced systemic and contact and leaf penetrating action against sucking insects, especially against insects of the Aphididae family (e.g. *Aphis fabae, Aphis craccivora* and *Myzus persicae*) which can only be controlled with difficulty using known pesticides.

The compounds of formula I also have a very useful action against flies such as *Musca domestica*, and mosquito larvae. Further, they have a broad ovicidal and ovolarvicidal action and have a useful action against ectoparasitic mites and ticks, e.g. of the Ixodidae, Argasidae and Dermanyssidae families.

The compounds of the formula I are used in unmodified form, or preferably together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the nature of the compositions, the methods of application such as spraying, atomising, dusting, scattering or pouring, are chosen in accordance with the intended objectives and the prevailing circumstances.

The formulations, i.e. the compositions or preparations containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers, and in some cases surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethyl sulfoxide or dimethyl formamide, as well as epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of the formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained, e.g. from coconut oil or tallow oil. Further suitable surfactants are also the fatty acid methyltaurin salts as well as modified and unmodified phospholipids.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate, or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$–$C_{22}$alkyl radical and, as further substituents, lower unsubstituted or halogenated alkyl, benzyl or lower hydroxyalkyl radicals. The salts are preferably in the form of halides, methylsulfates or ethylsulfates, e.g., stearyltrimethylammonium chloride or benzyldi-(2-chloroethyl)-ethylammonium bromide.

The surfactants customarily employed in the art of formulation are described e.g. in "McCutcheon's Detergents and emulsifiers Annual", MC Publishing Corp. Ringwood, N.J., 1979, and Dr. Helmut Stacke: "Tensid Taschenbuch", Carl Hanser Verlag, Munich/Vienna, 1984.

The pesticidal compositions usually contain 0.1 to 99%, preferably 0.1 to 95%, of a compound of the formula I, 1 to 99.9% of a solid or liquid adjuvant, and 0 to 25%, preferably 0.1 to 25%, of a surfactant.

Whereas commercial products are preferably formulated as concentrates, the end user will normally employ dilute formulations.

The compositions may also contain further ingredients, such as stabilisers, antifoams, viscosity regulators, binders tackifiers as well as fertilisers or other active ingredients for obtaining special effects.

FORMULATION EXAMPLES FOR LIQUID ACTIVE INGREDIENTS OF THE FORMULA I (THROUGHOUT, PERCENTAGES ARE BY WEIGHT)

| 1. Emulsifiable concentrates | (a) | (b) | (c) |
| --- | --- | --- | --- |
| active ingredient | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexane | — | 15% | 20% |
| xylene mixture | 65% | 25% | 20% |

Emulsion of any required concentration can be produced from such concentrates by dilution with water.

| 2. Solutions | (a) | (b) | (c) | (d) |
| --- | --- | --- | --- | --- |
| active ingredient | 80% | 10% | 5% | 95% |
| ethylene glycol monomethyl ether | 20% | — | — | — |
| polyethylene glycol 400 | — | 70% | — | — |
| N—methyl-2-pyrrolidone | — | 20% | — | — |
| expoxidised coconut oil | — | — | 1% | 5% |
| ligroin (boiling range 160–190°) | — | — | 94% | —% |

These solutions are suitable for application in the form of microdrops.

| 3. Granulates | (a) | (b) |
| --- | --- | --- |
| active ingredient | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 4. Dusts | (a) | (b) |
| --- | --- | --- |
| active ingredient | 2% | 5% |
| highly dispersed silicic acid | 1% | 5% |
| talcum | 97% | —% |
| kaolin | — | 90% |

Ready for use dusts are obtained by intimately mixing the carriers with the active ingredient.

FORMULATION EXAMPLES FOR SOLID ACTIVE INGREDIENTS OF THE FORMULA I (THROUGHOUT, PERCENTAGES ARE BY WEIGHT)

| 5. Wettable powders | (a) | (b) | (c) |
| --- | --- | --- | --- |
| active ingredient | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| 6. Emulsifiable concentrate | |
| --- | --- |
| active ingredient | 10% |
| octylphenol polyethylene glycol ether (4–5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| 7. Dusts | (a) | (b) |
| --- | --- | --- |
| active ingredient | 5% | 8% |
| talcum | 95% | — |
| kaolin | — | 92% |

Ready for use dusts are obtained by mixing the active ingredient with the carriers, and grinding the mixture in a suitable mill.

| 8. Extruder granulate | |
| --- | --- |
| active ingredient | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| 9. Coated granulate | |
|---|---|
| active ingredient | 3% |
| polyethylene glycol 200 | 3% |
| kaolin | 94% |

The finely ground active ingredient is uniformly applied, in a mixer, to the kaolin moistened with polyethylene glycol. Non-dusty coated granulates are obtained in this manner.

| 10. Suspension concentrate | |
|---|---|
| active ingredient | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

PREPARATORY EXAMPLES

Example 1

To prepare the starting material, a mixture of 15.6 g of nicotinic acid hydrazide, 70 g of triethyl orthoformate and a trace of potassium hydrogen sulfate is stirred for 2 hours at a bath temperature of 155° C., while continuously removing ethanol during the reaction. Excess ortho-ester is subsequently distilled off in a water jet vacuum. The starting material so obtained, 2-(3-pyridyl)-1,3,4-oxadiazole, has a melting point of 80°-82° C.

2-(3-Pyridyl)-1,3,4-thiadiazole

A mixture of 5.5 g of the above prepared 2-(3-pyridyl)-1,3,4-oxadiazole, 8.5 g of phosphorus pentasulfide and 70 ml of xylene is stirred for 16 hours at 150°-160° C. To the cooled reaction mixture are added 50 ml of water and stirring is continued for another 5 minutes. The reaction mixture is then filtered. The filter residue is taken up in 100 ml of 10% sodium hydroxide solution. After extraction with chloroform, the organic phase is washed with water, dried and concentrated. After purification by column chromatography over silica gel with a 95:5 mixture of chloroform/ethanol as eluant, the crude 2-(3-pyridyl)-1,3,4-thiadiazole (compound 1) of the formula

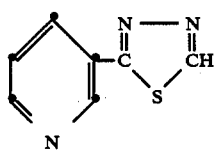

with a melting point of 64°-67° C., is obtained.

Example 2

To a solution of 22 g of N'-formylnicotinic acid hydrazide in 150 ml of pyridine are added, in portions, 28 g of phosphorus pentasulfide. During this addition the temperature rises to 65° C. After 5 minutes the mixture is heated to 110° C. and stirred for 2 hours at this temperature. The pyridine is then distilled off in a water jet vacuum. The residue is taken up in chloroform and the solution is extracted with a 5% sodium hydroxide solution and water. The organic phase is dried and the solvent is removed by evaporation, affording 2-(3-pyridyl)-1,3,4-thiadiazole as a pale yellow powder with a melting point of 78°-79° C.

Example 3

The compound of the formula

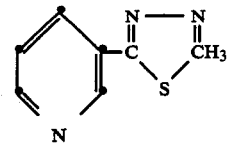 (compound 2)

with a melting point of 124°-126° C., and the compound of the formula

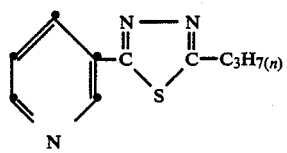 (compound 3)

with a melting point of 61°-63° C., are prepared by procedures similar to those described in Examples 1 and 2.

Example 4

6.22 g of hydroxylamino-O-sulfonic acid are added dropwise at 20° C. to a solution of 10.4 g of N'-(3-pyridyl)-thiocarbonyl-N,N-dimethylacetamidine in 200 ml of ethanol and 120 ml of methanol. The reaction mixture is stirred for 1 hour, then concentrated, and the residue is taken up in methylene chloride. The solution is extracted with 250 ml of water and 250 ml of 1N sodium hydroxide solution and dried over Na$_2$SO$_4$. The methylene chloride is distilled off and the residue is distilled at 100° C./0.035 Pa, affording the 5-(3-pyridyl)-3-methyl-1,2,4-thiadiazole (compound 4) of the formula

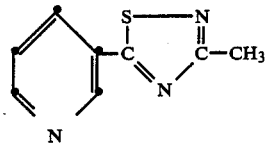

with a melting point of 65° C.

Example 5

Following the procedure of Example 4 and starting from N'-(3-pyridyl)thiocarbonyl-N,N-dimethylformamidine, the compound of the formula

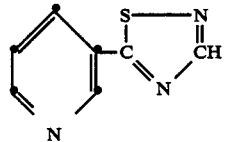 (compound 5)

with a melting point of 81°-83° C. is obtained.

BIOLOGICAL EXAMPLES

Example 6

Insecticidal systemic action in the soil against *Myzus persicae*

Cabbage plants which have grown roots are transplanted into pots which contain 60 ccm of soil. Then 50 ml of a solution containing respectively 0.75 ppm and 3 ppm of the test compound are poured direct onto the soil.

After 24 hours the parts of the plants above the soil are populated with aphids (*Myzus persicae*), and a plastic cylinder is then slipped over the plants to protect the aphids from any possible contact with the test substance, either directly or via the gas phase. A mortality count is made 48 hours and then 7 days after the start of the test. Two plants, each in a separate pot, are used for each test substance at its given concentration. The test is carried out at 25° C. and 70% relative humidity.

Compound 1 of Example 1 or 2 effects 80-100% kill against Myzus at 0.75 ppm. The compound is still 80-100% effective after 28 days at a concentration of 3 ppm.

Example 7

Insecticidal systemic action in water against *Aphis craccivora*

Pea plants which have been infested with the aphids 24 hours before the start of the test are put into 20 ml of an aqueous mixture which contains 12.5 ppm of the test compound. The aqueous mixture is prepared from an emulsifiable concentrate or from a wettable powder formulation of the test compound, and is contained in a vessel which is sealed with a perforated plastic top. The root of each infested pea plant is pushed into the mixture through a hole in the plastic top. The hole is then plugged with cotton wool in order to fix the plant and to prevent contact with the gas phase from the mixture. The test is carried out at 20° C. and 60% relative humidity. A mortality count of the test organisms is made after two days. Untreated controls are used for comparison purposes, in order to determine whether the test compound absorbed by the root kills the aphids on the upper parts of the plants.

In this test, compound 4 of Example 4 has an 80-100% systemic action (kill) against *Aphis craccivora* at 12.5 ppm.

Example 8

Insecticidal contact action against *Myzus persicae*

Pea plants which have been reared in water to a height of 4 cm are each populated with aobut 200 aphids of the species *Myzus persicae* before the start of the test. The treated plants are then sprayed dripping wet 24 hours later with an aqueous suspension containing the compound to be tested in a concentration of 100 ppm. Two plants are used for each compound at its given concentration. A mortality count is made 48 hours after application. The test is carried out at 20°-22° C. and 60% relative humidity. Compound 1 effects 80-100% kill at a concentration of 100 ppm.

Example 9

Insecticidal contact action against *Aphis craccivora*

Before the start of the test, bean plants (*Vicia faba*) which have been reared in pots are each populated with about 200 lice of the species *Aphis craccivora*. The treated plants are then sprayed dripping wet 24 hours later with an aqueous composition containing 50 and 100 ppm respectively of the test compound. Two plants are used for each compound at its given concentration and a mortality count is made 24 hours later.

80-100% kill is achieved with compounds 1, 2, 3 and 4 at 50 ppm and with compound 5 at 100 ppm.

Example 7

Insecticidal leaf penetration action against *Aphis craccivora*

A small shoot of *Vicia faba*, which is highly infested with aphids of the species *Aphis craccivora*, is placed in each of a number of 8 cm high plastic beakers (diameter about 6 cm). Each beaker is covered with a plastic lid having a punched opening of 2 cm diameter in the centre. A leaf of a *Vicia faba* plant is then placed over the opening in the lid without separating this leaf from the potted plant. The leaf is then fixed on the beaker with a second punched lid above the opening of the first lid. From underneath, i.e., through the opening of the first lid, the aphids in the beaker then infect the left of the plant used as bait. An aqueous formulation of the test compound is then applied in a concentration of 100 ppm uniformly with a brush to the top side of the leaf. An investigation is then made to determine whether the test substance applied to the top side of the leaf of the plant used as bait has diffused in sufficient amount through the leaf to its underside to kill aphids sucking thereon.

The test is carried out at about 20° C. and 60% relative humidity. The evaluation of percentage mortality is made 48 hours after application of the test compound.

Compounds 1, 2 and 4 effect 80-100% kill at 100 ppm.

What is claimed is:

1. A method of combating insects which attack plants, which method comprises applying to said plants or to the locus thereof an insecticidally effective amount of a compound of the formula I

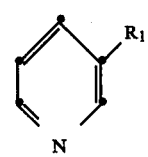

wherein $R_1$ is

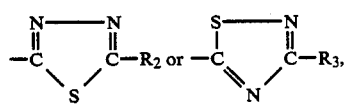

$R_2$ is hydrogen and $R_3$ is hydrogen or $C_1$-$C_4$alkyl.

2. A method according to claim 1, wherein $R_3$ in the compound of formula I is hydrogen or $C_1$-$C_3$alkyl.

3. A compound of the formula

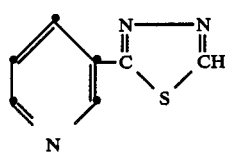

4. A method of combating insects which attack animals which method comprises applying to said pests or to said animals an insecticidally effective amount of a compound of the formula I

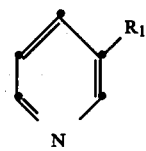 (I)

wherein $R_1$ is

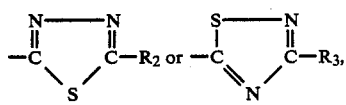

$R_2$ is hydrogen and $R_3$ is hydrogen or $C_1$-$C_4$alkyl.

5. A composition which comprises an insecticidally effective amount of a compound of the formula

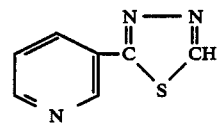

in combination with adjuvants customarily employed in insecticidally formulations.

* * * * *